(12) United States Patent
Molnar et al.

(10) Patent No.: US 11,813,467 B2
(45) Date of Patent: Nov. 14, 2023

(54) SYSTEMS, DEVICES AND METHODS FOR IMPLANTABLE NEUROMODULATION STIMULATION

(71) Applicant: SynerFuse, Inc., Minneapolis, MN (US)

(72) Inventors: Gregory F. Molnar, Blaine, MN (US); Nazmi Peyman, Glen Allen, VA (US); Kari W. Wright, Minneapolis, MN (US); Justin D. Zenanko, Minnetrista, MN (US); Beth A. Lindborg, St. Paul, MN (US); Kathleen W. Hill, St. Paul, MN (US); Kyle R. Grube, Minneapolis, MN (US); Michael C. Park, Excelsior, MN (US); Matthew A. Hunt, Minneapolis, MN (US)

(73) Assignee: SynerFuse, Inc., Minneapolis, MN (US)

( * ) Notice: Subject to any disclaimer, the term of this patent is extended or adjusted under 35 U.S.C. 154(b) by 867 days.

(21) Appl. No.: 16/665,525

(22) Filed: Oct. 28, 2019

(65) Prior Publication Data

US 2020/0129775 A1 Apr. 30, 2020

Related U.S. Application Data

(60) Provisional application No. 62/793,319, filed on Jan. 16, 2019, provisional application No. 62/752,223, filed on Oct. 29, 2018.

(51) Int. Cl.
*A61B 17/34* (2006.01)
*A61N 1/375* (2006.01)
(Continued)

(52) U.S. Cl.
CPC ...... *A61N 1/37518* (2017.08); *A61B 17/3421* (2013.01); *A61B 17/3468* (2013.01);
(Continued)

(58) Field of Classification Search
CPC ............ A61B 17/3468; A61B 17/3421; A61B 2017/3433; A61N 1/0551; A61N 1/36062; A61N 1/36071
See application file for complete search history.

(56) References Cited

U.S. PATENT DOCUMENTS

| 5,984,922 A | 11/1999 | McKay |
| 2010/0168808 A1 | 7/2010 | Citron |

(Continued)

FOREIGN PATENT DOCUMENTS

| WO | 2017/192486 A1 | 11/2017 |
| WO | 2018/017611 | 1/2018 |

OTHER PUBLICATIONS

International Search Report and Written Opinion issued in related PCT Application No. PCT/US2019/58428, dated Feb. 18, 2020.
(Continued)

*Primary Examiner* — Majid Jamialahmadi
(74) *Attorney, Agent, or Firm* — BARNES & THORNBURG LLP; Jeffrey R. Stone

(57) ABSTRACT

The present invention comprises implantable neuromodulation systems and methods comprising a protective pouch that at least partially encases an implantable pulse generator prior to implanting in a patient and is adapted to be secured within the surgical site. A lead placement tool configured to receive an electrical lead(s) along at least part of the length of the tool within an open channel or groove to assist in placing electrical leads at the desired target. The lead placement tool may have at least one, or two, angles that provide a bend or angle between first and/or second end regions relative to a straight central region and an open channel along at least one of these regions. A harness for receiving and protecting at least a portion of the length of electrical leads in operative communication with an implantable pulse
(Continued)

generator is provided. The harness is adapted to be secured within the surgical site.

9 Claims, 13 Drawing Sheets

(51) Int. Cl.
    *A61B 17/70*      (2006.01)
    *A61N 1/36*      (2006.01)
    *A61N 1/372*      (2006.01)
    *A61B 17/56*      (2006.01)

(52) U.S. Cl.
    CPC ...... *A61B 17/7001* (2013.01); *A61N 1/36062* (2017.08); *A61N 1/372* (2013.01); *A61B 2017/564* (2013.01)

(56) References Cited

U.S. PATENT DOCUMENTS

| | | |
|---|---|---|
| 2012/0277839 A1 | 11/2012 | Kramer et al. |
| 2013/0144356 A1 | 6/2013 | Horn et al. |
| 2014/0343673 A1 | 11/2014 | Matheny |
| 2016/0008514 A1 | 1/2016 | Jones |
| 2017/0319193 A1 | 11/2017 | Pulapura et al. |
| 2017/0319754 A1 | 11/2017 | Pulapura et al. |
| 2020/0061373 A1* | 2/2020 | Mitchell ............ A61B 17/3468 |
| 2021/0030408 A1 | 2/2021 | Sachs |

OTHER PUBLICATIONS

Extended Search Report issued by the European Patent Office for related application No. 19879554.4, dated Jun. 24, 2022.
Notification Concerning Transmittal of International Preiminary Report on Patentability and International Preliminary Report on Patentability issued in PCT/US2019/058428, dated May 14, 2021.

* cited by examiner

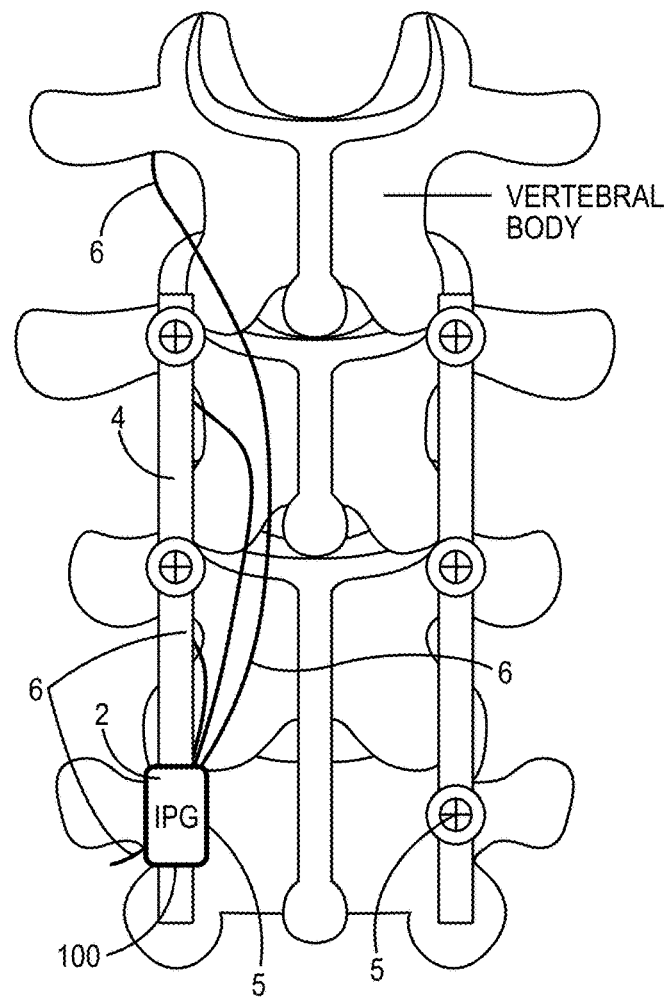 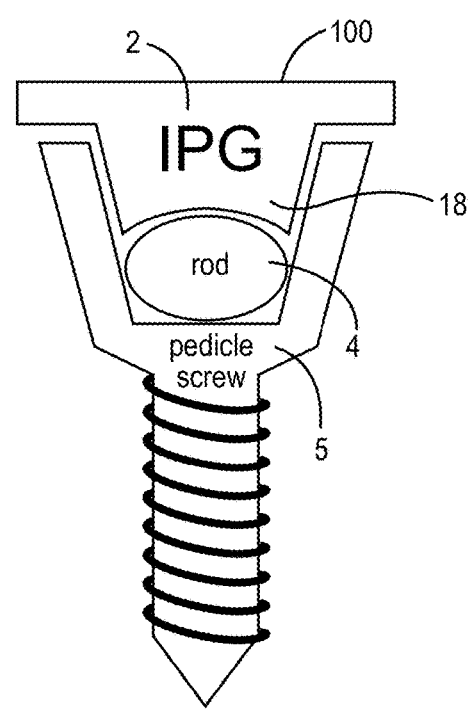
FIG. 5A  FIG. 5B

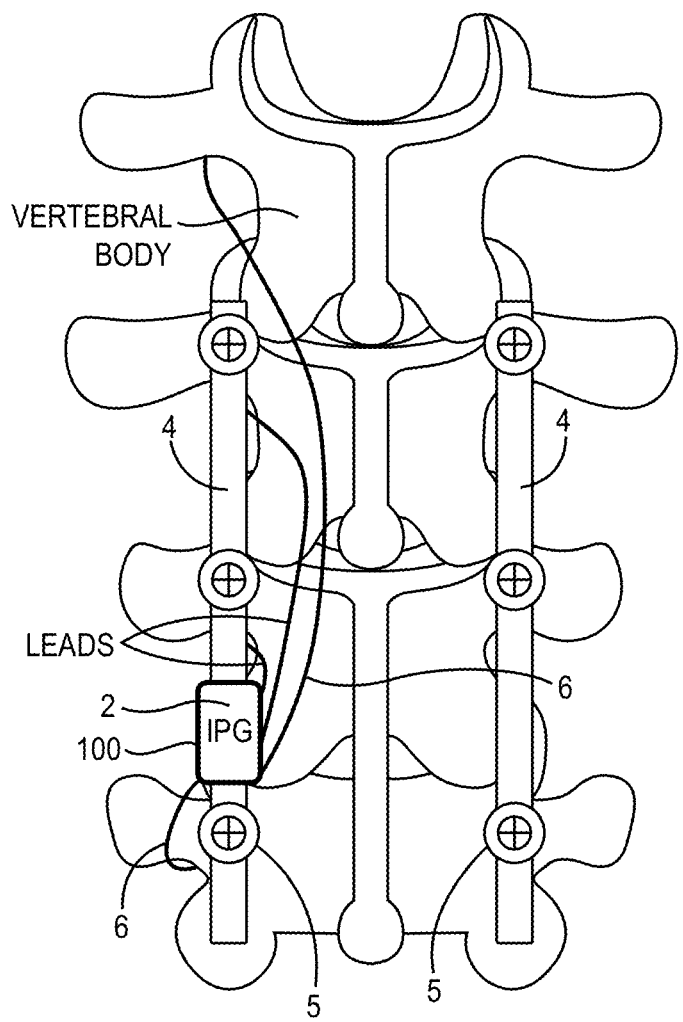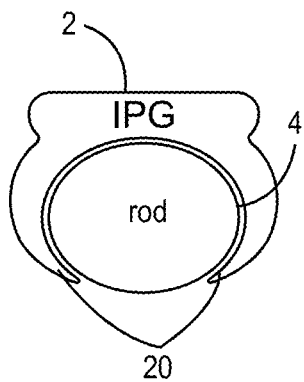
FIG. 6B
FIG. 6A

SYSTEMS, DEVICES AND METHODS FOR IMPLANTABLE NEUROMODULATION STIMULATION

CROSS-REFERENCE TO RELATED APPLICATIONS

This application claims priority to U.S. Provisional Patent Application No. 62/752,223, filed Oct. 29, 2018 and titled IMPLANTABLE NEUROMODULATION SYSTEM AND KIT and U.S. Provisional Patent Application No. 62/793,319, filed Jan. 16, 2019 and titled NEUROMODULATION THERAPIES AND IMPROVED NEUROMODULATION SYSTEMS, the contents of which are hereby incorporated by reference in their entirety.

STATEMENT REGARDING FEDERALLY SPONSORED RESEARCH OR DEVELOPMENT

Not Applicable

BACKGROUND OF THE INVENTION

Field of the Invention

The invention relates to a system and/or method for treating chronic spinal pain comprising a surgical procedure combining a spinal procedure such as vertebral fusion with implantation of a neuromodulation device, wherein the surgical procedure is conducted with open physical and visual access to the region of the spine undergoing treatment.

Description of the Related Art

A neuromodulation procedure in accordance with the present invention is performed at a spinal treatment site. The neuromodulation procedure includes the placement of one or more neurostimulation leads at one or more target spinal levels, and more specifically, at the dorsal root ganglia at each of the target spinal levels.

The neurostimulation leads include a distal portion having one or more electrodes positioned at the distal portion, the neurostimulation leads further having a proximal portion capable of coupling to an implantable pulse generator. The neurostimulation lead further includes one or more electrically conductive wires capable of receiving an electrical signal in a distal portion, when electrically coupled to a pulse generator. The neurostimulation leads, when coupled to an implantable pulse generator, are then capable of delivering an electrical signal via the electrodes to a target site, such as a target dorsal root ganglia.

The procedure for placing of the neurostimulation leads may include placing the distal segment of one or more neurostimulation leads at the corresponding one or more target dorsal root ganglia such that the one or more electrodes of the neurostimulation lead is in therapeutic proximity to the target dorsal root ganglia such that when the neurostimulation lead is coupled to an implantable pulse generator and an electrical signal is delivered to the target dorsal root ganglia via the implantable pulse generator such electrical signal results in neuromodulation of the target dorsal root ganglia.

The neuromodulation procedure may further include routing of the proximal portion of the neurostimulation lead to the implantable pulse generator. The implantable pulse generator may be placed during the spinal procedure in an anatomical location that is dependent upon the particular treatment procedure performed or dependent upon physician preference or dependent upon patient preference or some combination thereof.

Once the implantable pulse generator has been electrically coupled to the leads, the pulse generator can be activated to deliver, via the one or more neurostimulation leads, a neuromodulation therapy to the spinal treatment site.

Anchoring and/or securing the implantable pulse generator within the surgical site would be advantageous.

Anchoring and/or securing the electrical lead(s) along at least part of their length would be advantageous.

Providing an electrical lead placement tool to facilitate translation and placement of the electrode at the site of interest, e.g., in therapeutic proximity to a dorsal root ganglion, would be advantageous.

The Figures and the Detailed Description which follow more particularly exemplify these and other embodiments of the invention.

BRIEF DESCRIPTION OF THE SEVERAL VIEWS OF THE DRAWINGS

FIG. 5A is a top view of one embodiment of the present invention.

FIG. 5B is a side view of the embodiment of FIG. 5A.

FIG. 6A is a top view of one embodiment of the present invention.

FIG. 6B is a side view of the embodiment of FIG. 6A.

DETAILED DESCRIPTION OF THE INVENTION

The present invention provides a system and kit for improving and enhancing the implantation of a neuromodulation device alone or in combination with a spinal fixation or other spinal treatment procedure. The present invention further provides a system and kit for placing and anchoring the implantable pulse generator and leads at a spinal treatment site.

The present invention provides embodiments for a pouch for encasing an implantable pulse generator. The pouch having one or more attachment members for anchoring, tethering or fixating the pouch to a target anchor site. The present invention further provides embodiments of a tool for implanting a lead at a target nerve site, more specifically a target dorsal root ganglion.

The present invention further includes embodiments of a lead harness in combination with an attachment member for anchoring, tethering or fixating the harness to a target anchor site.

Various embodiments of the present invention may be implemented with implantation of a neuromodulation device or system, either alone or in combination with a spinal fixation or other spinal treatment procedure within a surgical site.

Figure 1A:
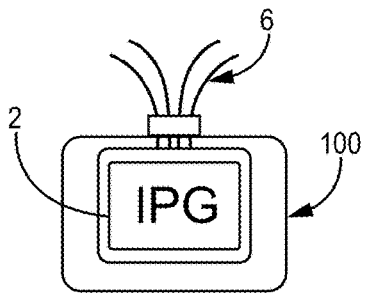
FIG. 1A is a view of one embodiment of the present invention.

FIG. 1A illustrates an implantable pulse generator (IPG) 2 with electrical leads 6 attached thereto. The IPG is at least partially enclosed in a pouch 100 and the leads 6 extend through the pouch 100 to the site of interest. The pouch 100 includes pouch walls W1, W2, W3 and/or W4, and/or W5, and/or W6 that may be defined relative to the implantable pulse generator 2. The pouch 100 includes first and second opposing walls W1 and W2, respectively, corresponding to the two major surfaces of the implantable pulse generator 2. The pouch 100 further includes one or more side-walls including any of walls W3-W6 extending between the two major surfaces and connecting the two opposing major surfaces W1 and W2 to each other. FIG. 1E provides an exemplary embodiment for pouch 100.

The pouch 100 walls W1-W6 may enclose all or only a portion of the corresponding side of the implantable pulse generator. As the skilled artisan will readily recognize, one or more of the side walls W3-W6 may be eliminated, wherein the major surface walls W1 and W2 are connected or integrated with each other directly. In the most extreme embodiment, Walls W1 and W2 are the only surfaces required. A sealable opening may be provided along one of the walls W1-W6 to allow insertion of the IPG 2 into the pouches interior defined by walls and then the opening may be sealed closed with the IPG 2 sealed inside.

One or more of pouch walls W1-W6 may further include one or more apertures A or discontinuities, including an aperture for allowing leads to extend through the pouch 100 wall and couple to the implantable pulse generator 2. Additional apertures A and discontinuities may be defined by the pouch wall in accordance with design preferences, functional benefits and application requirements. For example, without limitation, one or more apertures A or discontinuities may be incorporated into one or more pouch walls in order to allow tissue to anchor to the pouch when implanted in a patient's anatomy.

Alternatively, a continuous planar surface may be intentionally used on at least a portion of the pouch 100 to minimize tissue growth into, on or near that section of the pouch 1. As yet another alternative, one or more wall may be defined only by a narrow strip of pouch 100 material extending across a larger corresponding surface of the implantable pulse generator 2.

The pouch 100 has an interior space I defined by the pouch 100 walls W1, W2 and/or W3-W6, whether or not such pouch walls include one or more apertures A or discontinuities. The interior space defines a plenum for receiving an implantable pulse generator.

The interior space I may be dimensioned such that each wall W1, W2 and/or W3-W6 of the pouch 100 is in direct contact with a corresponding surface the implantable pulse generator 2 providing a snug fit around the IPG 2. Alternatively, only one or less then all of the interior surfaces of walls W1, W2 and/or W3-W6 of the pouch 100 may be in direct contact with the corresponding nearest surface of the implantable pulse generator 2, or such that only a portion of a given interior wall surface of the pouch 100 is in contact with a corresponding surface of the implantable pulse generator 2 to provide a loose fit.

The pouch 100 is made of a biocompatible material, such as medical grade silicone or other medical grade thermoplastic polymers capable of being implanted in a human anatomy. The properties of the pouch 100 may include a flexible, rubber-like attribute such that it is slightly to moderately deformable yet sufficiently rigid to maintain its general pouch shape. Suitable materials may include, but are not limited to, silicone rubber manufactured by Simtec at 9658 Premier Parkway, Miramar, Fla.

The pouch 100 may further be coated or impregnated with one or more chemicals or materials having additional biological and/or physiological activities or characteristics. Such attributes may include but are not limited to: antimicrobial, antifungal, antibiotic, anti-infection, analgesic properties, drug-eluting, tissue growth inhibiting, tissue growth enhancing, and combinations thereof.

The pouch 100, in accordance with the present invention, may be manufactured in various dimensions in order to define an interior surface capable of receiving an implantable pulse generator 2 having complimentary dimensions. There are many implantable pulse generators with varying dimensions and as such a pouch 100 may be dimensioned to the specific dimensions of a specific implantable pulse generator 2 or the pouch 100 may be dimensioned to approximately enclose a wide range of implantable pulse generators. Alternatively, the pouch 100 may be adjustable along one or more dimensions in order to accommodate implantable pulse generators of different dimensions.

Figure 1B:
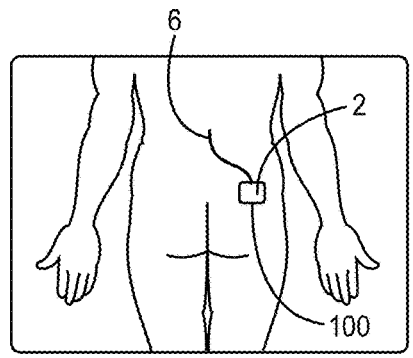
FIG. 1B is a view of the embodiment of FIG. 1A implanted into a patient's anatomy.
Figure 1C:
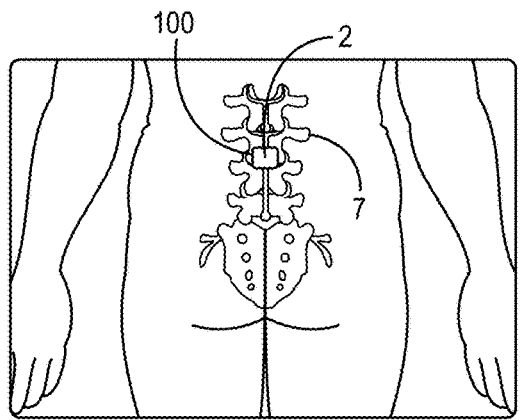
FIG. 1C is a view of the embodiment of FIG. 1A implanted into a patient's anatomy.
Figure 1E:
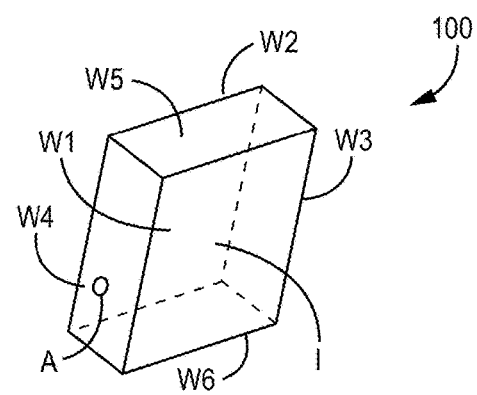
FIG. 1E is a perspective view of one embodiment of the present invention.
Figure 1D:
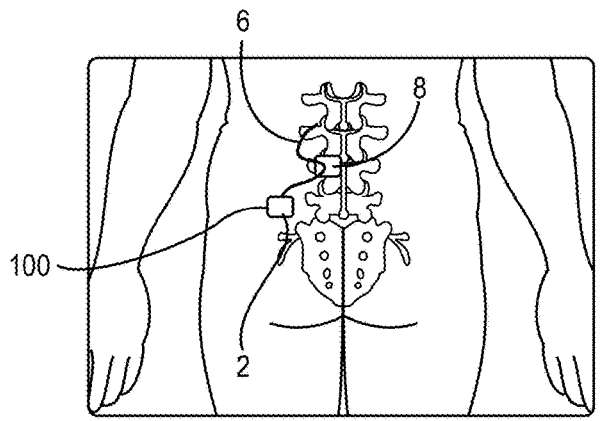
FIG. 1D is a view of the embodiment of FIG. 1A implanted into a patient's anatomy.

As shown in FIGS. 1B-1D, the pouch 100 may be used in conjunction with an implantable pulse generator 2 implanted to provide a neuromodulation therapy to one or more target dorsal root ganglia. Such an implantable pulse generator 2 may be substantially smaller in size than implantable pulse generators traditionally used in spinal cord stimulation. Specifically, the implantable pulse generator 2 shown in FIGS. 1B-1D may have a volume of 11 cubic centimeters, or between 3 cubic centimeters and 10 cubic centimeters, or between 1 cubic centimeters and 3 cubic centimeters, or less than 1 cubic centimeter. As such, the pouch 100 may be dimensioned such that an interior surface defines a shape and volume corresponding to that of the implantable pulse generator 2.

As shown in FIG. 1B, an implantable pulse generator 2 may be received within a pouch 100 and the combination results in a pouch-encased implantable pulse generator 2, or at least partially encased or enclosed within the pouch 100. The pouch-encased implantable pulse generator 2 may be implanted in the tissue of the patient anatomy located at the flank as generally shown in FIG. 1B. As described, the implantable pulse generator 2 may be completely or partially enclosed or encased within pouch 100.

As shown in FIG. 1C, a pouch-encased implantable pulse generator 2 may be implanted along the spine 7 of a patient anatomy. The pouch-encased implantable pulse generator 2 may be implanted at a section of the patient anatomy where bone has been removed from the spinal treatment site, or it may be implanted next to, at, or near an existing spinal process of the patient anatomy.

As shown in FIG. 1D, a pouch 100 encased implantable pulse generator 2 may be implanted remotely from a spinal treatment site. A junction box 8 may, in some embodiments, be implanted at or near the spinal treatment site and leads extend from the junction box 8 to the remotely positioned pouch 100 encased implantable pulse generator 2. Alternatively, junction box 8 may be operatively electrically connected with IPG 2 with leads 6 extending from junction box 8 to the site of interest, e.g., a dorsal root ganglion.

The pouch-encased implantable pulse generator 2 may be implanted by a variety of methods and sequences. The pouch-encased implantable pulse generator 2 may be implanted during and in combination with an open back spinal fixation, or other spinal, procedure, prior to or after such spinal procedure has been completed, as a procedure independent of a spinal procedure, as a minimally invasive procedure and/or as part of a revision procedure.

Figure 2:
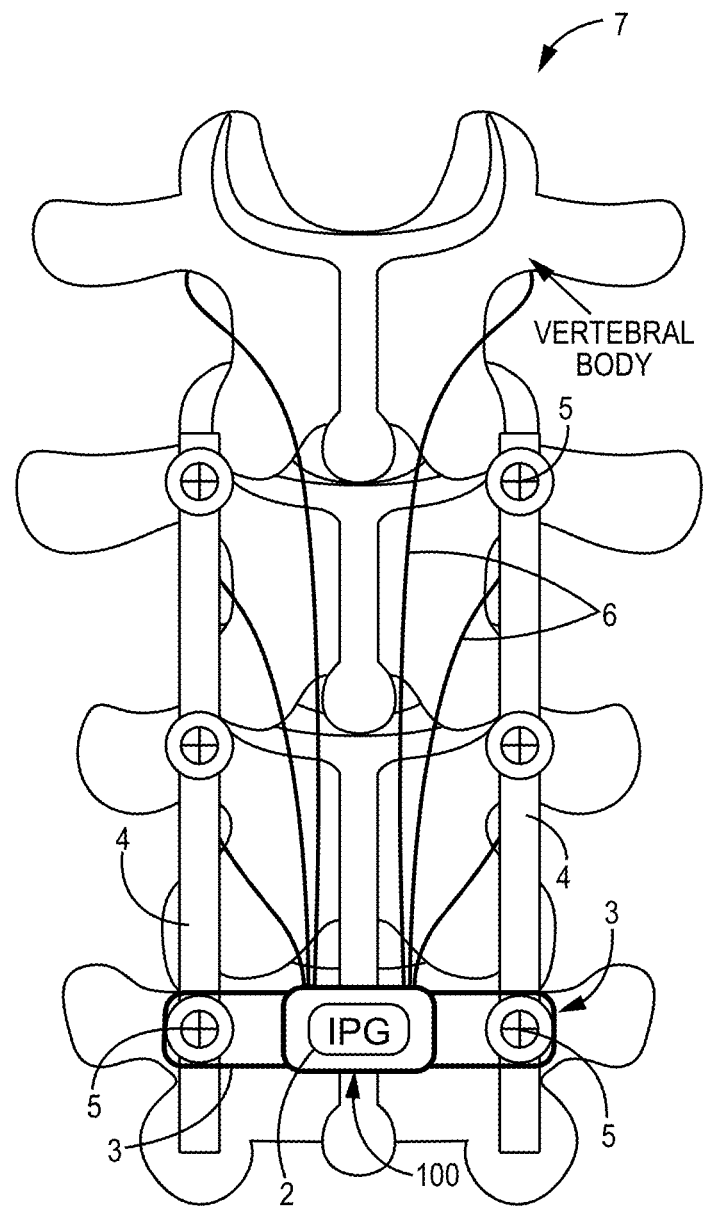
FIG. 2 is a top view of one embodiment of the present invention.

FIG. 2 shows an implantable pulse generator 2 encased in a pouch 100 as described above and implanted over the spine 7 of a patient anatomy at a spinal treatment site. The implantable pulse generator 2 is dimensioned such that it is positioned at a spinal treatment site between a pair of spinal fixation rods 4 for fixing relative motion between affected vertebrae. The implantable pulse generator 2 may be positioned between two existing spinous processes or in the bone removed portion of a spinal treatment site.

The pouch 100 at least partially encasing the implantable pulse generator 2 may include one or more attachment elements for anchoring the pouch 100 to a corresponding one or more spinal fixation rods 4. The attachment elements in the present embodiment may comprise non-rigid looped attachment members 3 that extend from the pouch 100 to a remotely positioned pedicle screw 5. The non-rigid looped attachment members 3 comprise a flexible medical grade material having elastic rubber-band like properties such that the attachment members provide a releasable tension that allows for connecting of the pouch 100 to the pedicle screw 5 by looping a portion of the attachment member around the pedicle screw 5.

When the non-rigid looped attachment members 3 are operatively connected to and/or looped around the pedicle screw 5, the pouch 100 is maintained in a tethered relationship to the pedicle screw 5 by the tension in the portion of the non-rigid looped attachment member 3 extending from the pedicle screw 5 to the pouch 100. The pouch 100 may be attached to two separate pedicle screws 5 via separate attachment members 3 or separate portions of a single tension member such that it is maintained in relative position to the spinal fixation rods 4.

Figure 3A:
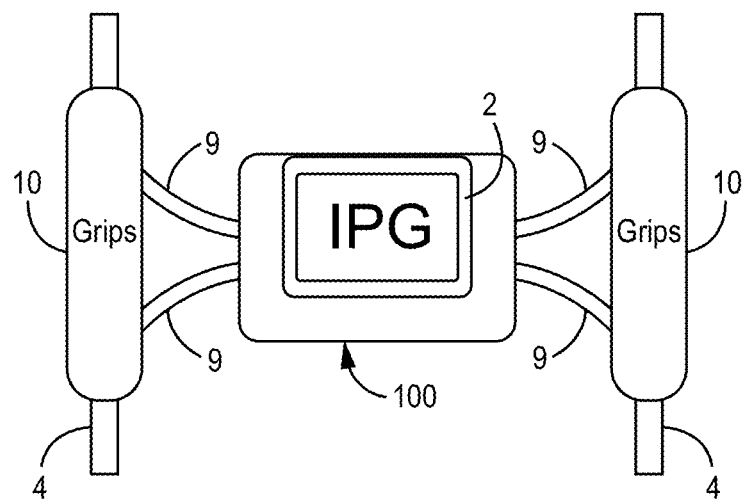
FIG. 3A is a top view of one embodiment of the present invention.
Figure 3B:
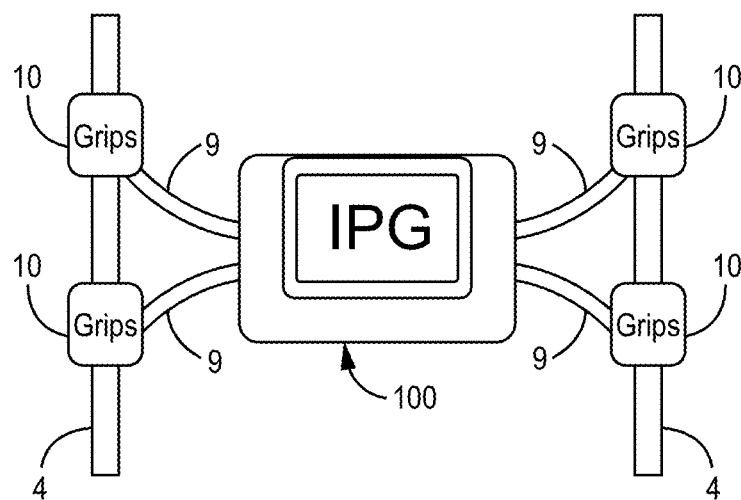
FIG. 3B is a top view of one embodiment of the present invention.

FIGS. 3A and 3B show an implantable pulse generator 2 at least partially encased in a pouch 100 as described above and positioned between a pair of spinal fixation rods 4. The pouch may include one or more attachment elements or tethers 9 extending from a first end, or a wall W1-W6 as shown in FIG. 1E, at the pouch 100 to a second end, or a wall W1-W6, coupled to a spinal fixation rod 4. The second end of the attachment element or tether 9 may be coupled to the spinal fixation rod 4 with a grip 10 for maintaining a connection between the second end of the attachment element or tether 9 and the corresponding spinal fixation rod 4.

In FIG. 3A a first single grip 10 is shown attached to a single corresponding first fixation rod 4, two attachment members or tethers 9 extend from a first end at the pouch 100 to a second end at the first single grip 10 to tether the pouch 100 to the first fixation rod 4.

A second single grip 10 is shown attached to a single corresponding second fixation rod 4. Two attachment members or tethers 9 extend from a first end at the pouch 100 to a second end at the second single grip to tether the pouch 100 to the second fixation rod 4.

In FIG. 3B, four separate attachment members or tethers 9 are shown, each extending from a first end at the pouch 100 to a second end at a corresponding grip 10 to couple the pouch 100 to the corresponding first and second fixation rods 4 in a generally X-type relationship.

The attachment elements or tethers 9 in FIGS. 3A and 3B may be flexible and elastic in performance so as to maintain a tension between the first and second end of the attachment member or tether 9 when extending between the pouch 100 and grips 10.

Alternatively, the attachment members or tethers 9 may be non-flexible or minimally flexible and merely tether the pouch 100 to the fixation rod 4 without providing tension therebetween.

Whether the attachment elements or tethers 9 are flexible/elastic or non to minimally flexible, the pouch 100, and encased implantable pulse generator 2, will be anchored between the fixation rods 4 but will be able to float within a predetermined volume of space to a greater or lesser extend depending upon the flexibility and slack of the attachment elements or tethers 9.

Figure 4:
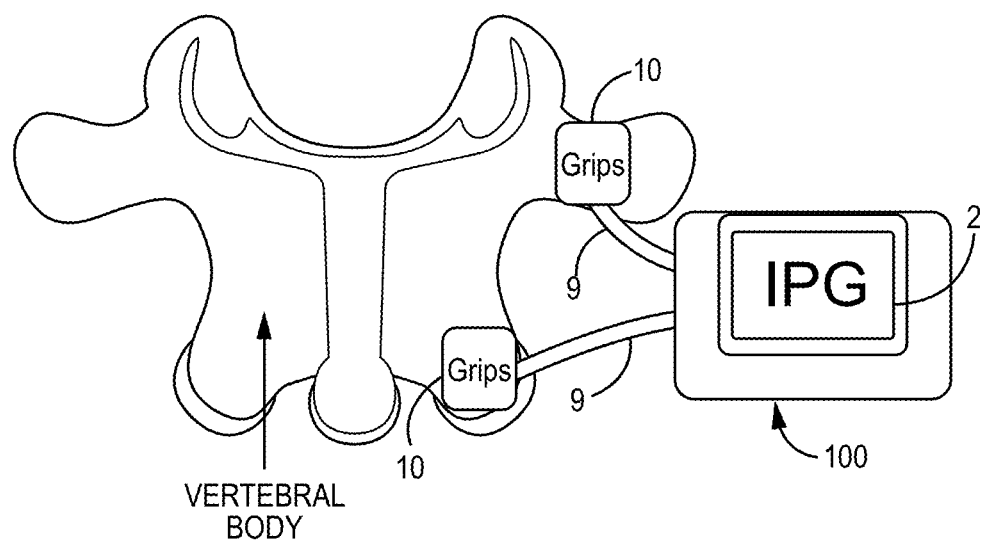
FIG. 4 is a top view of one embodiment of the present invention.

FIG. 4 illustrates an implantable pulse generator 2 encased in a pouch 100 as described above. The pouch-encased implantable pulse generator 2 may be positionable next to the vertebral body of a spinal treatment site as shown, or between adjacent vertebral bodies of a spinal treatment site. One or more attachment elements or tethers 9 as described above are shown having a first end extending from the pouch 100 and a second end extending to a grip 10, also as described above. However, in this embodiment, the attachment elements or tethers 9 provide a tethered fixation of the pouch 100 to a portion of a vertebral body, instead of a fixation rod 4, by grip 10 coupled to the second end of the attachment element 9. The attachment elements or tethers 9, when engaged with a vertebral body by corresponding grips 10, maintain the pouch 100 encased implantable pulse generator 2 in a tethered relationship with respect to the vertebral body. This feature also allows our implantable pulse generator device to be implanted and fixated by a surgeon independent of any spinal fixation components. This could also be delivered and fixated by way of a minimally invasive spinal surgical approach.

FIGS. 5A-5B illustrate a pouch 100 encased implantable pulse generator 2 wherein the pouch 100 includes an attachment surface 18 extending from a portion of the pouch 100 for attaching the pouch 100 to a pedicle screw 5. The attachment surface 18 may comprise one or more contoured side walls configured to mate with a corresponding receiving wall of the pedicle screw 5 head. The connecting element further includes a contoured end wall configured to engage a portion of a fixation rod 4. The attachment surface 18 shown in FIGS. 5A and 5B maintains the pouch 100 encased implantable pulse generator 2 in a fixed relationship with respect to the pedicle screw 5 to which it is attached.

FIGS. 6A-6B illustrate a pouch 100 encased implantable pulse generator 2 wherein the pouch 100 includes an attachment member 20 extending from a portion of the pouch body for attaching the pouch to a fixation rod. The attachment member 20 includes an outwardly extending connecting element having a contoured and/or complementary engagement surface for engaging the outer surface of a fixation rod 4. The attachment member 20 shown in FIGS. 6A and 6B maintains the pouch 100 encased implantable pulse generator 2 in a fixed relationship with respect to the fixation rod 4 to which it is attached.

FIGS. 1A through 6B relate to implantation and fixation of the implantable pulse generator 2 using a pouch 100 for encasing the implantable pulse generator 2 and one or more attachment elements or surfaces for fixating the pouch 100 encased implantable pulse generator 2 within a patient's anatomy.

Figure 7A:
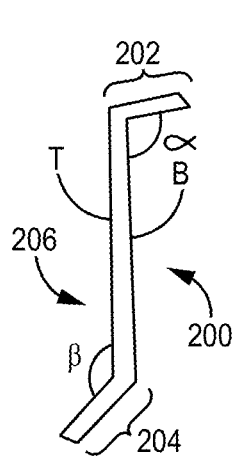
FIG. 7A is a side view of one embodiment of the present invention.
Figure 7B:
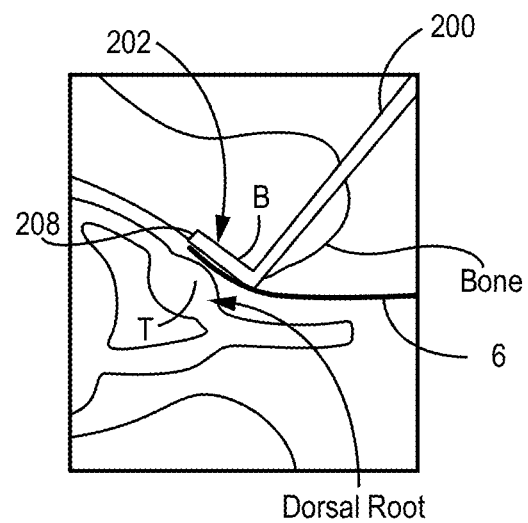
FIG. 7B is a top view of the embodiment of FIG. 7A.
Figure 7C:
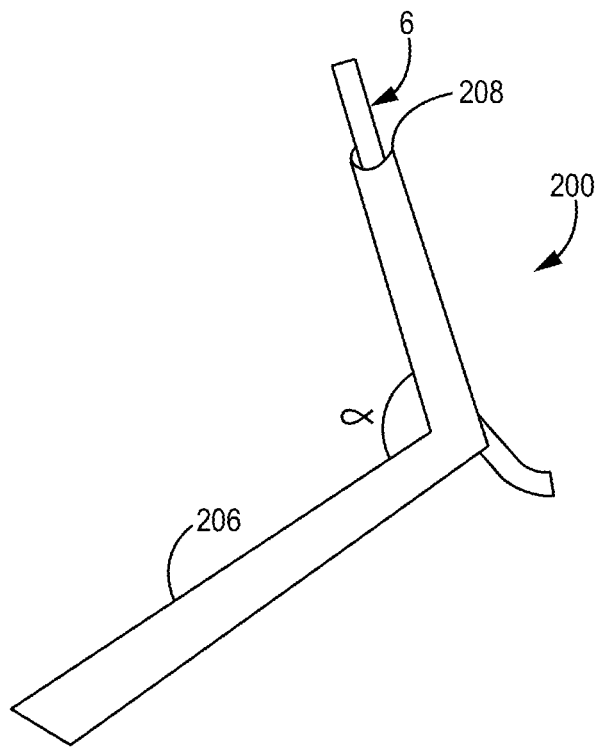
FIG. 7C is a side view of one embodiment of the present invention.
Figure 7D:
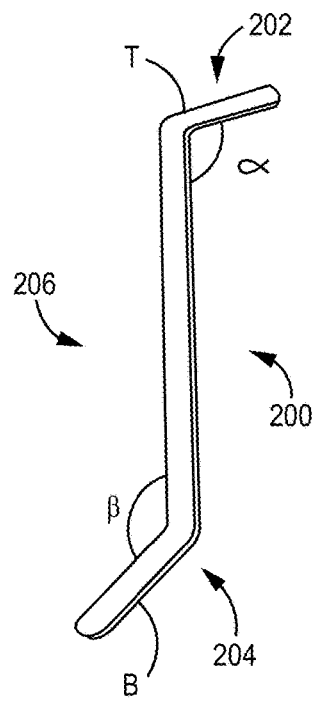
FIG. 7D is a perspective view of one embodiment of the present invention.
Figure 7E:
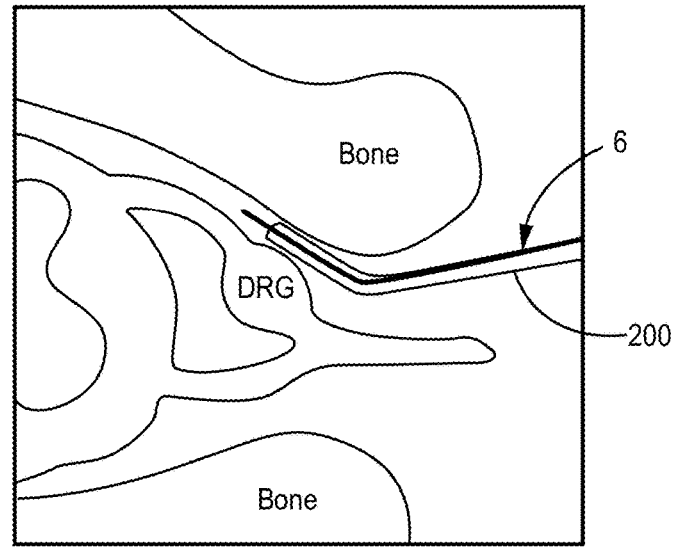
FIG. 7E is a side view of one embodiment of the present invention.
Figure 7F:
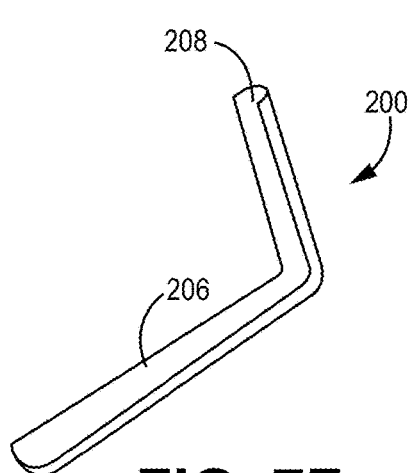
FIG. 7F is a perspective view of one embodiment of the present invention.
Figure 7G:
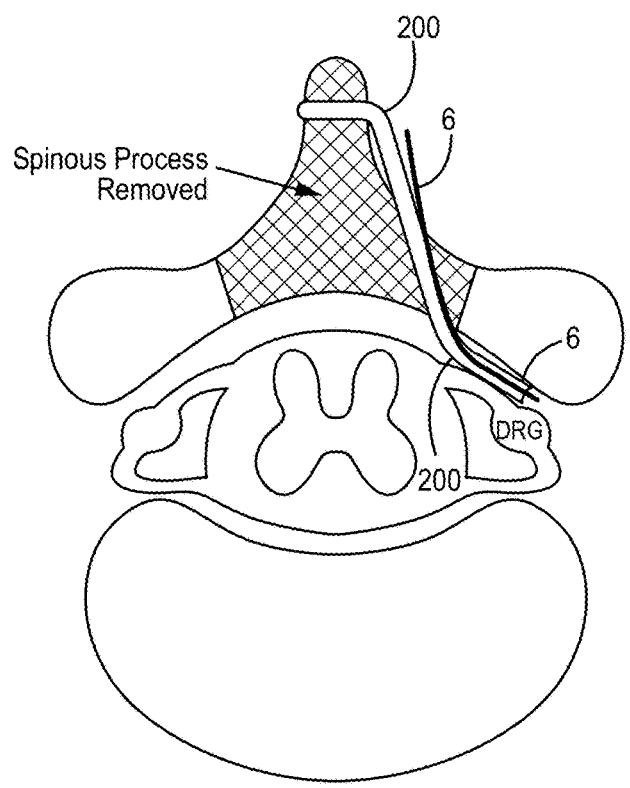
FIG. 7G is a perspective view of one embodiment of the present invention.
Figure 8:
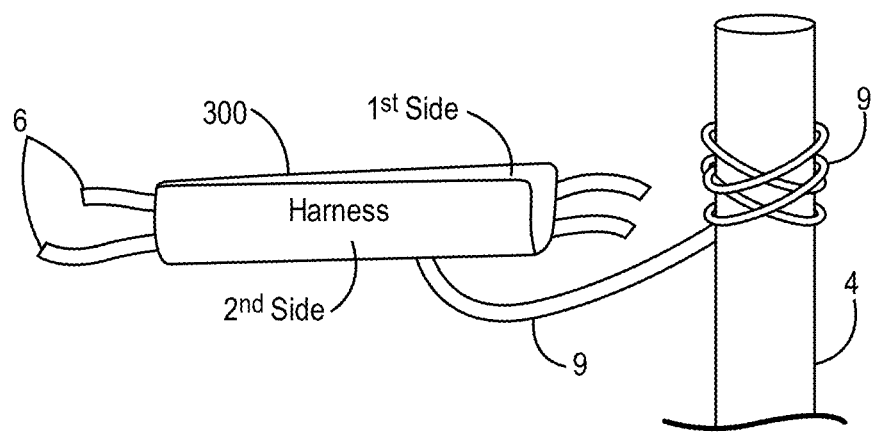
FIG. 8 is a side view of one embodiment of the present invention.

FIGS. 7-9 relate to lead placement and fixation in a patient anatomy.

FIGS. 7A-7C illustrate a lead placement tool 200. The lead placement tool 200 comprises first and second end regions, 202, 204 and a central region 206 extending therebetween, and a top surface T and a bottom surface B extending along first and second regions 202, 204 and central region 206. The first end region 202 of the lead placement tool 11 may have an angle α, as shown about a 90-degree bend, with respect to the central portion 206 of the tool 200. The first end region 202 of the lead placement tool 200 may comprise a portion that is curved to create a groove or channel 208 that is open for slideably receiving a lead 6 therein. The first end 202 of the lead placement tool 200 further has a bottom surface B for slideably advancing and retracting the lead placement tool 200 against a bone or other anatomical space. FIG. 7C shows an exemplary groove or channel 208 with electrical lead received therein. As will be discussed below, first or second regions 202, 204 may be straight, without a bend relative to the central region 106.

As shown, and in all embodiments, the first and second regions, 202, 204 and the central region 206 of the lead placement tool 200 all extend along a common longitudinal plane, whether angles exist or not. In other words, the first and second regions 202, 204 and the central region 206 are collinear and coplanar.

The groove or channel 208 may be provided alone one or both of first and second end regions 202, 204. Further, the groove or channel 208 may be disposed so that is it open along the top surface of one or both of first and second end regions 202, 204 and/or open along the bottom surface of one or both of first and second end regions 202, 204.

As shown in more detail in FIG. 7B, the first end region 202 of the lead placement tool 202 is positioned in an anatomical space such that the bottom surface B of the lead placement tool 200 interfaces with the bone and the top surface of the first end region of the tool 200 provides the open groove or channel 208 for slideably advancing the lead 6 for placement at an anatomical site such as the dorsal root ganglia or in therapeutic proximity to the dorsal root ganglia or other nerve target. Once the lead 6 has been placed in therapeutic proximity to the dorsal root ganglia or other nerve target, the lead placement tool 200 can then be slideably retracted, leaving the lead 6 in place.

The second end region of the lead placement tool 11, as shown in FIG. 7A, may have an angle β with respect to the axis of the central region 206 of the tool 200, creating an exemplary angle of about 45 degrees between the second end region 204 and the central region 206. The second end region of the tool 11 may have a curved open portion creating a groove or channel 208 similar to that of the first end region 202. The groove or channel 208 when present in either first or second end regions 202, 204 may be formed along the top surface T of tool 200, the bottom surface B of tool 200. The first end region 202 may comprise the groove or channel 208 along its top surface T or its bottom surface B and the second end region 204 may comprise the groove or channel 208 along its top surface or its bottom surface B.

In all cases, the surface of the tool 200 that is opposite of the open groove or channel 208 is curved, closed and relatively smooth to allow that portion of the tool 200 to slide along bone or other anatomical structure.

In some cases only a single angle and groove or channel 208 may be provided. In other embodiments, two angles and two grooves or channels 208 are provided.

The second end region 204 of the tool 200 functions in the same manner as described above with respect to the first end of the tool 200. The angles α and β may be the same or they may differ. Depending on patient anatomy and/or the preference of the physician performing the lead placement procedure, the first end region 202 or the second end region 204 of the tool 200 may be the more preferable and/or more effective guide for lead placement in a given procedure or procedure step.

It is intended that the 90-degree bend and 45-degree bend described with respect to the first end region 202 and second end region 204, respectively, are merely exemplary, and that many different bend angles are contemplated in accordance with the present invention even extending as far as a straight tool with a zero-degree bend, and including a shallow bend tool 200 with at least one end region having a less than 45-degree bend with respect to the axis of the central region 206 of the tool 200

FIGS. 7D-7G illustrate an alternative embodiment of a lead placement tool 200. The tool 11 has opposing first and second end regions 202, 204 and a central region 206 extending therebetween. The first end region 202 of the lead placement tool 200 comprises angle α that is shown about a 90-degree bend with respect to the central region 200 of the tool 200.

The first and second end regions 202, 204 of the lead placement tool 200 has top surface T curved to create a groove or open channel 208 for slideably receiving a lead 6 therein. As noted, alternative embodiments may comprise groove or open channel 208 formed along the bottom surface B of tool 200.

As best shown in FIGS. 7E-7G, open channel 208 may extend beyond either the first end or second end regions 202, 204 and may extend along a top T or bottom B surface of the central region 206 in certain embodiments.

Returning to FIGS. 7D-7G, once the lead 6 has been placed in therapeutic proximity to the dorsal root ganglia or other nerve target, the lead placement tool 200 can then be slideably retracted, leaving the lead 6 in place at or near the nerve target.

Depending on patient anatomy and/or the preference of the physician performing the lead placement procedure, the first end or the second end regions 202, 204 of the lead placement tool 200 may be the more preferable and/or more effective guide for lead placement in a given procedure or procedure step. It is intended that the illustrated 90-degree bend and 45-degree bend for angles α and/or β are merely exemplary, and that many different bend angles are contemplated in accordance with the present invention even extending as far as a straight tool 200 with a zero-degree angle between the first or second end region and the central region, and further includes a shallow angle embodiment with at least one of the first or second regions having a less than 45-degree bend with respect to central region of the tool 200.

FIG. 8 illustrates a lead harness 300 having a first side for receiving one a portion of one or more leads 6 thereon. The lead harness 300 is flexibly foldable such that the first side forms a channel for slideably maintaining the portion of the leads 6 therein. The second side of the lead harness 12 forms a protective cover over the portion of the leads 6 maintained within the channel formed by the first side.

The harness 300 further includes an attachment member 9 having a first end connected to and extending from the harness 300 and a second end extending to and connectable to an anchor location. The anchor location may be a fixation rod 4 as shown in FIG. 8 or may be a bone or tissue or a pedicle screw 5 or any other element that would be sufficient to maintain position of the attachment member 9. The attachment member 9 may be a flexible material such that it forms a tethered relationship between the anchor location and the harness 300, providing some degree of movement to the harness 300 but only within a tethered area defined by the attachment element 9.

The second end of the attachment member 9 may be connected to the fixation rod 4 by wrapping the second end of the attachment member 9 around the fixation rod 4 and/or tying the second end to the fixation rod 4. Any number of attachment mechanisms may be used in combination with the attachment member 9 to connect the attachment member 9 to an anchor site include a suture, a twist tie, a gripper, a coil and other such attachment mechanisms.

The harness 300 provides the advantage of maintaining the placement and positioning of the leads 6 with respect to each other without providing a gripping force that could be damaging to the lead body and that could potentially lead to loss of performance or functionality of the lead 6.

The harness 300 and harness attachment member 9 in combination with the pouch 100 and pouch attachment member 9, and the various embodiments of these, provide a means for maintaining the positioning of the implantable pulse generator 2 and the leads 6 in anatomical positions that allow for the ongoing delivery of neuromodulation therapy.

Figure 9A:
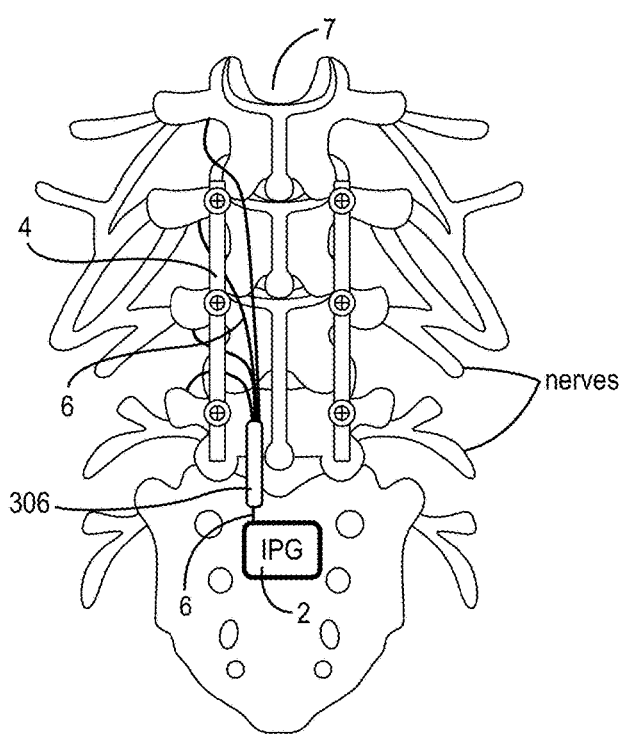
FIG. 9A is a top view of one embodiment of the present invention.
Figure 9B:
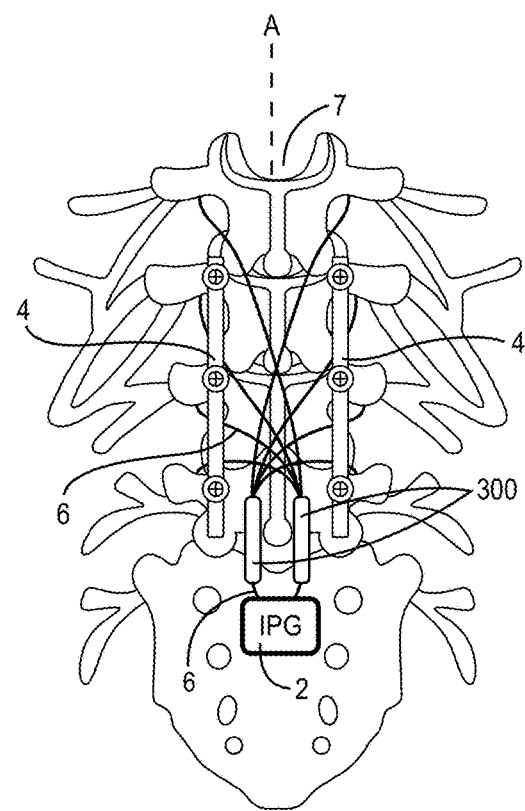
FIG. 9B is a top view of one embodiment of the present invention.

FIGS. 9A and 9B provide example embodiments of the lead placement and lead harness 12 of a neuromodulation system implanted in a patient anatomy in accordance with the present invention.

FIG. 9A shows a series of leads 6 placed such that a distal end of each lead is positioned in therapeutic proximity to a corresponding dorsal root ganglion, each lead 6 at a different nerve level. The proximal end of each lead 6 converges such that the proximal end of each lead 6 is received in the lead harness 300 resulting in a unilateral arrangement of the leads 6 and lead harness 300.

FIG. 9B illustrates a bilateral arrangement of leads 6 and corresponding lead harnesses 300. A first set of leads 6 each have distal ends on a single side of a patient spine 7, each lead 6 being placed at a different nerve level in therapeutic proximity to a corresponding dorsal root ganglia. The proximal portions of the first set of leads 6 cross the spinal axis and converge to enter a lead harness 300 on the opposite side of the spinal axis A. A second set of leads 6 is in a mirrored relationship to the first set of leads 6, each of the second set of leads 6 having a distal end positioned at a different nerve level, placed in therapeutic proximity to a corresponding dorsal root ganglia. The proximal end of each of the second set of leads 6 crossing the spinal axis A and converging to enter a lead harness 300 on the opposite side of the spinal axis A. This bilateral arrangement of lead placement with respect to lead harness 300 positioning may provide additional lead placement stability by minimizing the bending forces on the distal ends of the lead 6 while the harness 300 provides additional lead fixation support.

Both FIGS. 9A and 9B provide the lead placement and a spinal fixation device with fixation rods 4 and pedicle screws 5.

Figure 10A:
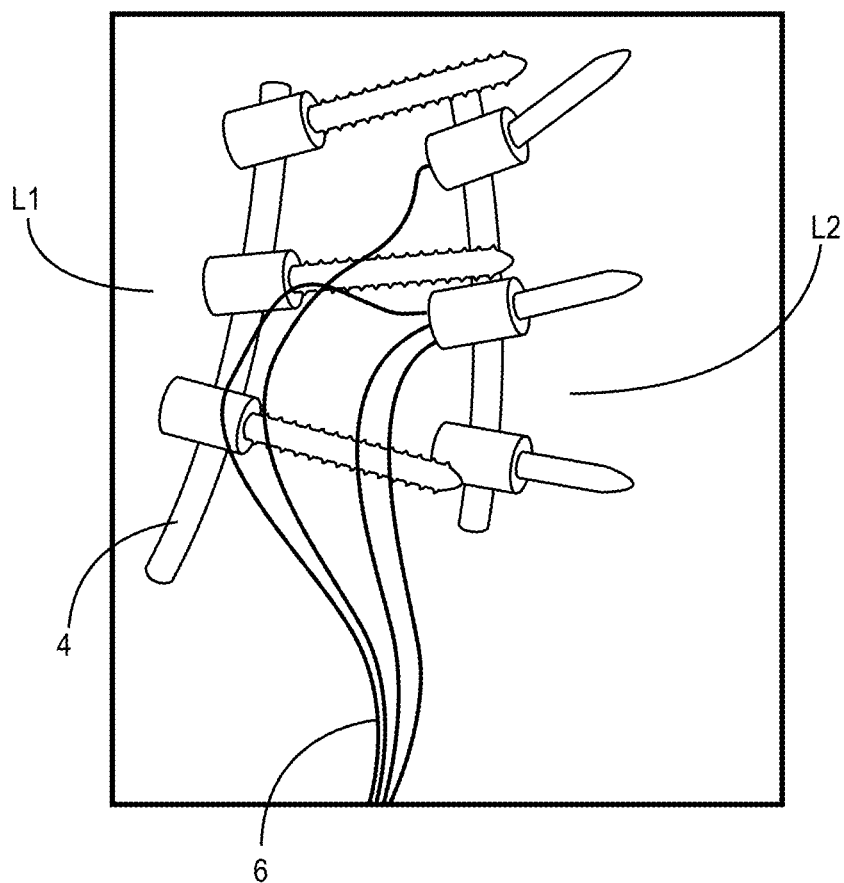
FIG. 10A is a fluoroscopic image of one embodiment of the present invention.
Figure 10B:
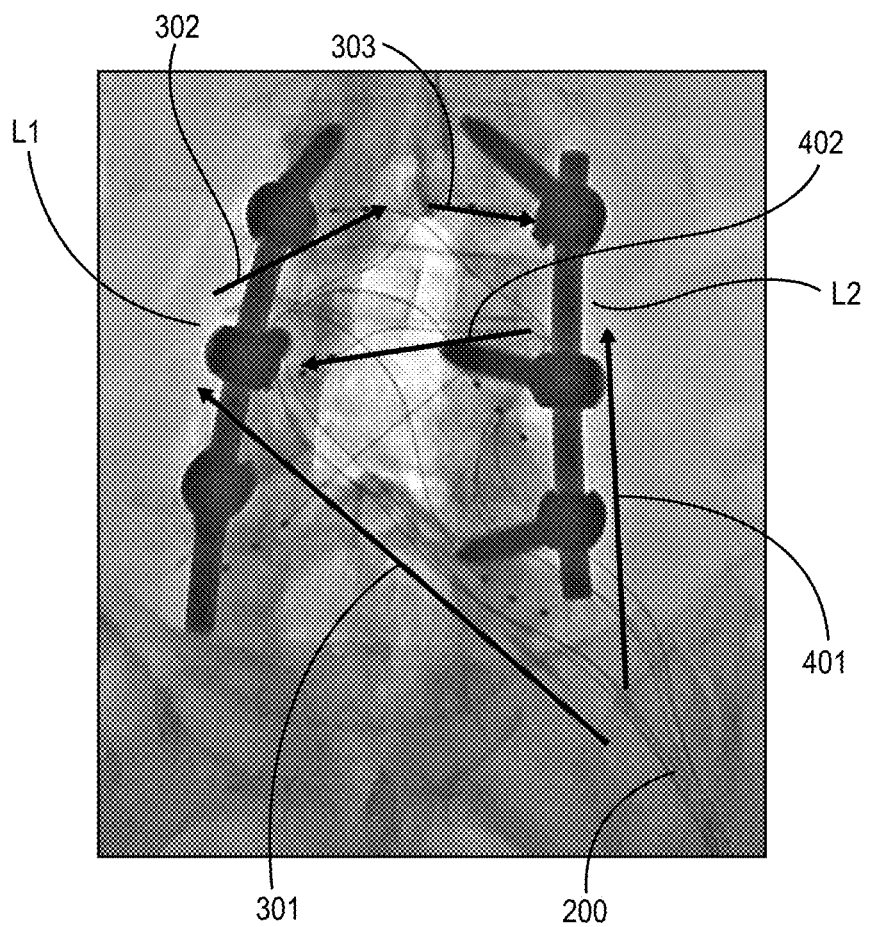
FIG. 10B is a fluoroscopic image of one embodiment of the present invention.

FIGS. 10A-10B are fluoroscopic images of leads 200 implanted at a spinal treatment site in combination with a spinal fixation implant. FIG. 10A shows a spinal treatment site where the spinous process bones have been removed during implant of the spinal fixation device. The leads 6 were delivered from a medial (over the spinal cord dura) to lateral pathway approach through to the spinal foramen and the treatment site at the DRG. As shown, the leads 6 enter medially and then flare out to opposing first or second lateral sides, loop around a portion of the spinal fixation device and extend to a neuromodulation target at an opposite first or second lateral side of the treatment site such that each lead 6 is in therapeutic proximity to a corresponding dorsal root ganglia. By way of example, lead enters medially and extends to a first lateral side L1, loops around a portion of the spinal fixation device on the first lateral side L1 and then crosses to the opposing second lateral side L2 for placement in therapeutic proximity to the target dorsal root ganglia.

FIG. 10B shows a spinal treatment site where the bone has been removed during implant of the spinal fixation device. The leads extend from a single unilateral approach at a spinal level below the fixation device. The leads are then placed along a pathway 301, 302, 303 such that leads placed on unilateral approach side are curved around an opposing lateral side of the fixation device and back across the spinal treatment site to a corresponding target dorsal root ganglia. The leads placed on the opposing lateral side are curved around a portion of the fixation device on the unilateral approach side before extending laterally to the opposing lateral side via pathway 401, 402.

The lead placement tool 200 described herein can be used, by way of example, for placement and anchoring of leads in accordance with the lead pathways shown in FIGS. 10A-10B and with any other such lead pathway as determined by such factors that may include but are not limited to patient anatomy, bone structure, whether bone has been removed, physician preference, lead properties, position of the implantable pulse generator and other considerations.

The lead harness 300 can be used, by way of example, at the location where a single lead may require anchoring to ensure that a therapeutic relationship is maintained between the lead and the target nerve. The lead harness 300 may additionally be used, by way of example but not limiting other uses, at a location where two or more leads converge such as shown in FIGS. 10A-10B.

Figure 11:
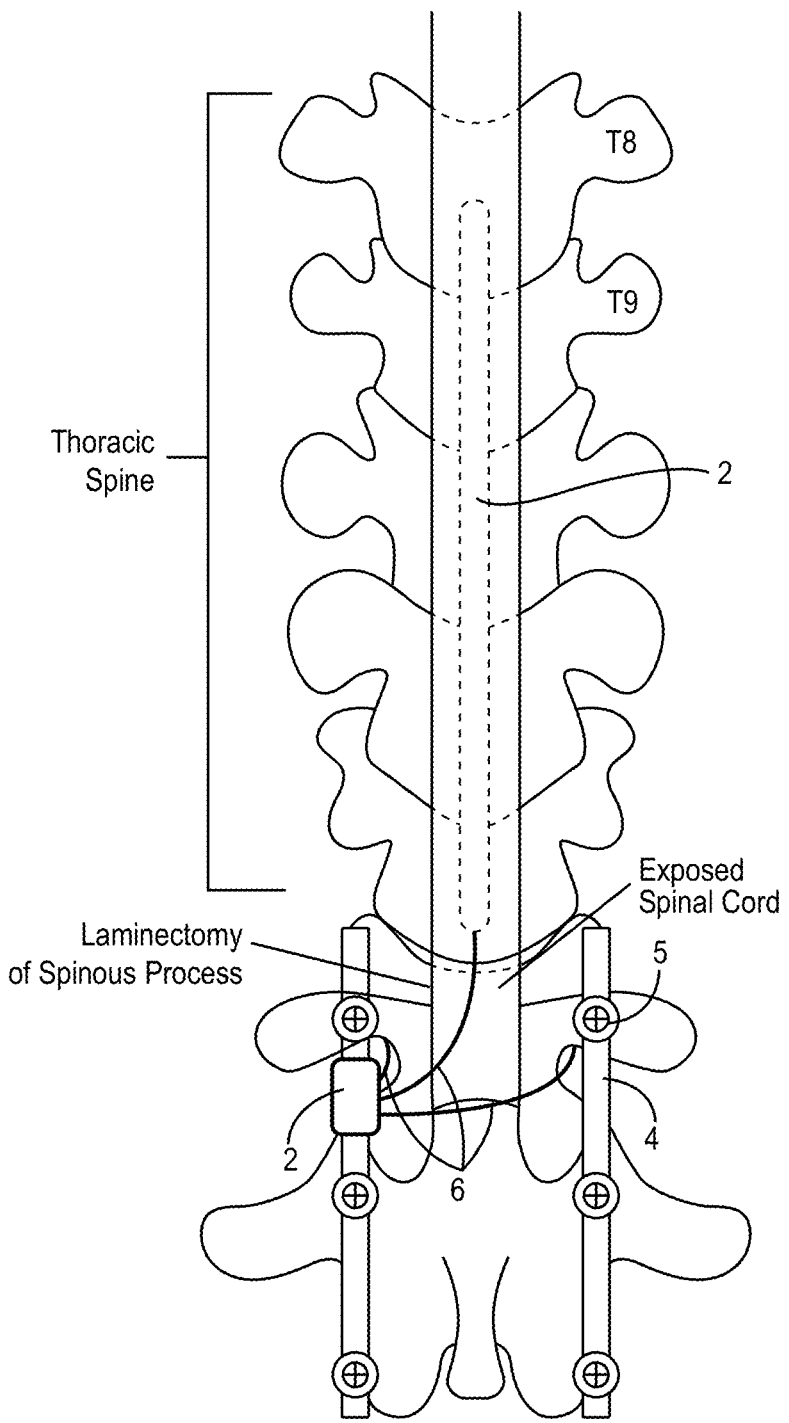
FIG. 11 is a top view of one embodiment of the present invention.

FIG. 11 illustrates an embodiment of a neuromodulation system including an implantable pulse generator 2 and one or more neurostimulation leads 6 coupled to the implantable pulse generator 2. The neuromodulation system 13 is implanted at a spinal treatment site where a spinal procedure has been performed including a decompression procedure and/or including a spinal fixation procedure. As shown in FIG. 11, the neuromodulation system is implantable in combination with a spinal fixation procedure including one or more spinal fixation rods 4 secured to the spinal treatment site by pedicle screws 5. The implantable pulse generator 2 and leads of the neuromodulation system 13 may incorporate any of the previously described features and elements, or variations thereof, as described above, including but not limited to a pouch 100, various attachment elements coupled to the pouch 100 to anchor or secure the pouch-enclosed IPG, and may incorporate a lead harness 300.

As shown in FIG. 11, the lead 6 is positioned along the spinal cord to provide a neurostimulation signal to the spinal cord. The lead 6 extends from the spinal treatment site at a portion of the spinal treatment site where the spinal cord was exposed during a spinal treatment procedure. The lead 6 is positioned along a lead pathway that extends to at least a portion of the thoracic spine, under the intact spinous process of the portion of the thoracic spine. The lead 6 may be incorporate a spinal cord stimulation paddle lead design having one or more programmable electrodes for optimization of spinal cord stimulation.

Although not shown in FIG. 11, one or more leads 6 may additionally extend from the implantable pulse generator 2 to one or more target dorsal root ganglia in accordance with the various lead pathways previously described above.

Another method for implanting a neuromodulation system incorporated herein is a lateral approach to neurostimulation. Neuromodulation and delivering electrical or other forms of energy have been typically performed from the dorsal aspect of the spinal cord. Another approach has been through the neuroforamena and the dorsal root ganglion.

There are many pathways including but not limited to spinothalamic tract that run in the anterolateral and anterior part of the spinal cord. These nerve fibers and tracts carry a variety of information including pain signals to more central locations and the brain. Performing spinal cord stimulation from a lateral and/or anterolateral and anterior approach has been anatomically and practically challenging. Current lead designs and placement techniques may also cause sensation of pain by the patient.

The improved method for lateral placement of a lead 6 incorporates a lead 6 that will be placed in the lateral and/or anterolateral and/or anterior part of the epidural space in the thoracic and/or lumbar and/or cervical region to deliver electrical energy using a variety of frequencies including but not limited to high frequencies and a variety of complex stimulation patterns.

Other modes of neuro-modulation including pulsed radiofrequency, cooling or gentle heat may also be applied with this approach. The electrode/electrodes may also collect a variety of data and biometrics as well as delivering energy. For example cordotomy has been used in extreme refractory cases of cancer pain in the past. It includes lesioning the spinothalamic tract which produces pain relief with significant side effects, namely dysesthesias, apnoea and urinary retention. Placing an anterior lead could be an attempt to modulate and not destroy these nerve fibers and achieve the relief without these serious side effects.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A lead placement tool for placement of an electrical lead within a spinal treatment site having access to one or more target spinal levels for delivering neuromodulation stimulation to at least one dorsal root ganglion within the spinal treatment site, the lead tool comprising:
   first and second end regions and a central region disposed therebetween, the lead tool adapted for routing and placing the electrical lead in therapeutic proximity with a dorsal root ganglion;
   wherein at least a part of the first end region comprises a first partially open channel and adapted to translatingly receive the electrical lead therein, and
   wherein the lead tool is angled at a point between the central portion and the first region, wherein the central region, the first end region and the second end region are disposed along a common longitudinal plane,
   wherein at least a part of the second end region of the lead placement tool comprises a second partially open channel adapted to translatingly receive the electrical lead therein, and wherein the lead placement tool is angled at a point between the central region and the second end region, wherein the central region, the first end region and the second end region are disposed along the common longitudinal plane of the lead placement tool.

2. The lead placement tool of claim 1, wherein the lead tool comprises a top surface and a bottom surface and wherein the first partially open channel is open along the top surface.

3. The lead placement tool of claim 1, wherein the lead tool comprises a top surface and a bottom surface and wherein the first partially open channel is open along the bottom surface.

4. The lead placement tool of claim 1, wherein the lead placement tool comprises a top surface and a bottom surface and wherein the second partially open channel is open along the top surface of the lead placement tool.

5. The lead placement tool of claim 1, wherein the lead placement tool comprises a top surface and a bottom surface and wherein the second partially open channel is open along the bottom surface of the lead placement tool.

6. The lead placement tool of claim 1, wherein the lead placement tool comprises a top surface and a bottom surface and wherein the first partially open channel and the second partially open channel are both open along the top surface of the lead placement tool.

7. The lead placement tool of claim 6, wherein the central region comprises a third partially open channel that is open along the top surface of the lead placement tool.

8. The lead placement tool of claim 6, wherein the central region comprises a third partially open channel that is open along the bottom surface of the lead placement tool.

9. The lead placement tool of claim 1, wherein the lead placement tool comprises an top surface and bottom surface and wherein the first partially open channel and the second partially open channel are both open along the bottom surface of the lead placement tool.

* * * * *